United States Patent [19]
Burg et al.

[11] Patent Number: 5,437,990
[45] Date of Patent: Aug. 1, 1995

[54] SELECTIVE AMPLIFICATION OF TARGET POLYNUCLEOTIDE SEQUENCES

[75] Inventors: James L. Burg, Foster City; Philippe J. Pouletty, Menlo Park; John C. Boothroyd, Palo Alto, all of Calif.

[73] Assignee: The Board of Trustees of the Leland Stanford Junior University, Stanford, Calif.

[21] Appl. No.: 121,034

[22] Filed: Sep. 13, 1993

Related U.S. Application Data

[63] Continuation of Ser. No. 623,255, Dec. 5, 1990, abandoned, which is a continuation of Ser. No. 80,479, Jul. 31, 1987, abandoned.

[51] Int. Cl.[6] .................... C12P 19/34; C07H 21/02; C07H 21/04
[52] U.S. Cl. .................... 435/91.2; 435/91.1; 435/91.21; 435/91.3; 435/91.5; 435/91.51; 436/501; 536/22.1; 536/23.1; 536/25.3; 935/88
[58] Field of Search ............. 435/6, 91.1, 91.2, 91.21, 435/91.3, 91.32, 91.4, 91.41, 91.5, 91.51, 810; 436/501; 536/22.1, 25.3, 23.1, 24.3, 24.31-24.33; 935/77, 78, 88

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,130,238 | 7/1992 | Malek et al. | 435/91 |

OTHER PUBLICATIONS

Mullis, Kary B.; slide of May 1986 talk at the University of California Berkley.
Guatelli et al. Proc Natl Acad Sci 87:1874-78 (1990).
Genetic Engineering News Jun. 1992 pp. 1, 8 & 9.
Melton et al. Nuc Acids Res 12(18) pp. 7035-7056 (1984).
V. D. Axelrod et al., Transcription from Bacteriophage T7 and SP6 RNA Polymerase Promoters in the Presence of 3'-Deoxyribonucleoside 5'-Triphosphate Chain Terminators, Biochemistry (1985) 24:5716-5723.

*Primary Examiner*—Margaret Parr
*Assistant Examiner*—Ardin H. Marschel
*Attorney, Agent, or Firm*—Cooley Godward Castro Huddleson & Tatum

[57] ABSTRACT

A method is provided for multiplying the number of copies of a target polynucleotide sequence comprising a series of primer hybridization, extending, and denaturing steps to provide an intermediate double-stranded DNA molecule containing a promoter sequence (through the use of a promoter-sequence-containing primer) incorporated upstream from the target sequence. The double-stranded DNA intermediate is then used to grow multiple RNA copies of the target sequence. The resulting RNA copies can be used as target sequences to produce further copies. Multiple cycles of this sort can thereby exponentially increase the number of target sequence copies.

10 Claims, 1 Drawing Sheet

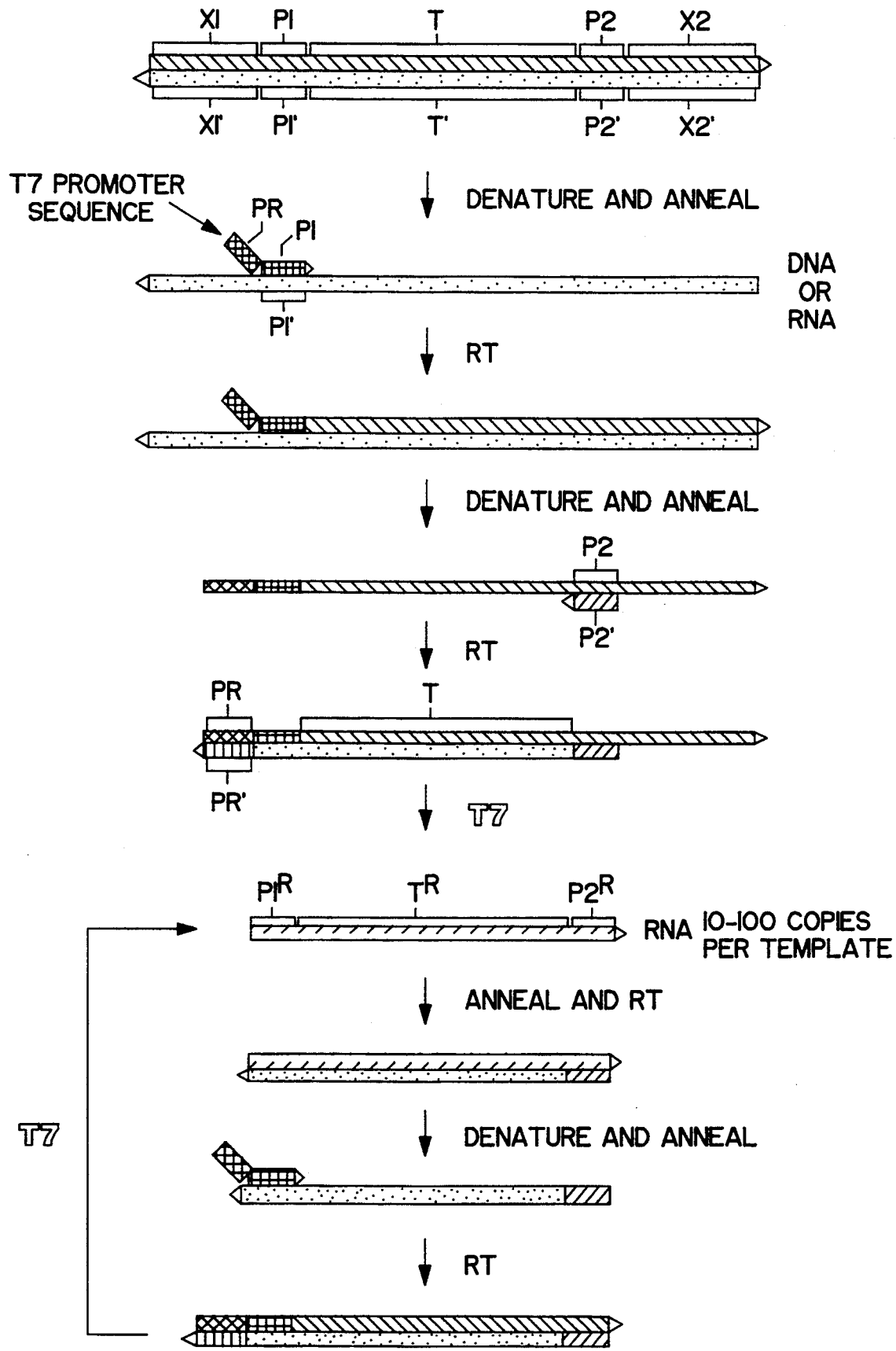

SELECTIVE AMPLIFICATION OF TARGET POLYNUCLEOTIDE SEQUENCES

This invention was made with Government support under a grant awarded by the National Institutes of Health. The Government has certain rights in the invention.

CROSS REFERENCE TO RELATED APPLICATIONS

This application is a continuation of U.S. patent application Ser. No. 07/623,255, filed Dec. 5, 1990, now abandoned, which is a continuation of U.S. patent application Ser. No. 07/080,479, filed Jul. 31, 1987, now abandoned.

FIELD OF THE INVENTION

This invention is related to diagnostic assays in which the presence of a particular gene is being detected, whether for detection of the gene itself or detection of the organism containing the gene, and is particularly directed to techniques in which the number of copies of the gene being detected is enzymatically increased prior to the detection process. It is further related to any process requiring the generation of many copies of a specific polynucleotide sequence.

BACKGROUND OF THE INVENTION

A number of diagnostic assays have been developed which rely on detection of the presence of a particular DNA or RNA sequence as an indication of the presence of an analyte, e.g., a bacterium, virus, or genetic defect, in a sample. In some cases the diagnostic gene is present in sufficient quantities to be detected directly, whether by hybridization, reaction with a specific antibody, or by some other method. However, if the gene of interest is present in a small amount or the background caused by similar sequences present in the sample is sufficiently high, reliable and sensitive detection of the targetted gene is difficult. An ambiguous result is not satisfactory in a diagnostic test.

Various techniques for increasing the sensitivity and specificity of such diagnostic procedures have been developed. Amplification of the target by cell culture, an efficient but time consuming technique, has been for long the only reliable method. Other techniques increase sensitivity of the detection system using sensitive reporter groups attatched to the probe which will combine with the target. Examples of sensitive reporter groups would include radioactive and fluorescent molecules. Enzymes, such as peroxidase or alkaline phosphatase coupled to the probe, also improve sensitivity through their catalytic action on substrate chromophores. Increased sensitivity may also be obtained by an amplification of the reporter groups. Such amplification has been achieved through avidin-biotin interactions, networking with nucleic acids, or the direct enzymatic replication of an RNA reporter group. This latter technique generates up to 1,000,000 copies of the RNA in about 12 minutes. Another technique amplifies the target nucleic acid sequence rather than the reporter groups used in the detection system.

One method for amplification of target nucleic acid is known as the polymerase chain reaction or PCR technique and has been developed for detecting the genes responsible for genetic defects. This method uses specific oligonucleotide primers in repeated cycles of target DNA denaturation, primer annealing, and extension with a DNA polymerase. Extension products generated from one primer serve as additional target sequences for the other primer. The degree of amplification of a target sequence is controlled by the number of cycles that are performed and is theoretically calculated by the simple formula $2^n$ where n is the number of cycles. Given that the average efficiency per cycle ranges from about 65% to 85%, 25 cycles are needed to yield from 0.3 to 4.8 million copies of the target sequence.

Although the polymerase chain reaction is a very sensitive and promising method, there are some limitations and disadvantages inherent in this technique. For example, each cycle of polymerase chain reaction provides at best only a 2-fold amplification, and thus a high number of cycles (between 20 and 30) is required to achieve substantial amplification. Furthermore, the high-temperature denaturation that occurs in each PCR cycle typically inactivates the enzyme used and thus requires repeated addition of expensive enzyme.

Accordingly, techniques that increase the rate of gene amplification (thereby requiring less enzyme and fewer cycles) would be highly advantageous to all diagnostic techniques that involve the detection of a specific target nucleotide sequence and any other procedure needing an increased number of specifically amplified polynucleotides (RNA or DNA).

RELEVANT LITERATURE

The PCR method is described in a number of publications, including Saiki et al., "Enzymatic amplification of beta-globin genomic sequences and restriction site analysis of sickle cell anemia" *Science* (1985) 230:1350–1354; Saiki et al., "Analysis of enzymatically amplified beta-globin and HLA-DQ alpha DNA with allele-specific oligonucleotide probes", *Nature* (1986) 324:163–166; and Scharf et al., "Direct cloning and sequence analysis of enzymatically amplified genomic sequences" *Science* (1986) 233:1076–1078 Also see European Patent Application publication no. 0 200 362 A2 (Application No. 86302298-4), published December 10, 1986, which claims priority to three U.S. patent application Ser. No. 716,975, filed March 28, 1985; U.S. patent application Ser. No. 791,308, filed Oct. 10, 1985; and U.S. patent application Ser. No. 828,144, filed Feb. 7, 1986.

SUMMARY OF THE INVENTION

The present invention provides a method for rapidly multiplying (through an enzymatic cycle) the number of copies of a target polynucleotide sequence by alternating two procedures that make copies from a target template. In a first series of steps, an intermediate double-stranded polynucleotide is produced comprising a promoter followed by the target sequence. The double-stranded intermediate is then used in a second process to prepare multiple RNA copies using an RNA polymerase that binds to the promoter region of the double-stranded intermediate. Each of the RNA copies can then be used as a target sequence to initiate another amplification cycle by preparing a second (or further) collection of double-stranded promoter-containing intermediates using reverse transcriptase. The process of the invention therefore provides a technique that multiplies in vitro the number of copies of a target polynucleotide sequence present in a sample much faster than prior processes. The method is applied in a specific embodiment to a diagnostic assay for *Toxoplasma gondii*.

BRIEF DESCRIPTION OF THE DRAWING

The present invention will be better understood by reference to the following detailed description of the invention when considered in combination with the drawing that forms part of the specification, wherein:

The Figure is a schematic diagram showing polynucleotides present at different stages of the method of the invention.

DESCRIPTION OF SPECIFIC EMBODIMENTS

The present invention provides a method for multiplying the number of copies of a target polynucleotide sequence and therefore is particularly useful in diagnostic assays intended to recognize specific polynucleotide sequences that are present in small amounts in a sample. It is also useful in any method benefitting from rapid generation of polynucleotides of specific sequence.

The target polynucleotide sequence may be only a fraction of a larger molecule or can be present initially as a discrete molecule, so that the specific sequence constitutes the entire nucleic acid. It is not necessary that the target sequence to be amplified be present initially in a pure form. It can be a minor fraction of a complex mixture, such as a portion of a nucleic acid sequence due to a particular microorganism, which organism constitutes only a minor fraction of a particular biological sample being analyzed.

The starting reaction mixture containing polynucleotides can contain more than one target sequence if desired. Therefore, the present process is useful not only for producing large amounts of one specific polynucleotide target sequence but also for amplifying simultaneously more than one different target sequence located on the same or different polynucleotide molecules. If more than one target sequence is present, the only modification required of the present invention is to provide primers (discussed below) for each of the desired target sequences.

Any specific polynucleotide target sequence can be amplified by the present process. It is only necessary that a sufficient number of nucleotides at both ends of the sequence be known in sufficient detail so that two oligonucleotide primers can be prepared as described below. The greater the knowledge about the bases at both ends of the sequence, the greater can be the specificity of the primers for the target sequence, and thus the greater the efficiency of the process. It will be understood that the word primer as used herein can refer to more than one primer, particularly in the case where there is some ambiguity in the information regarding the terminal sequence or sequences of the target to be amplified. For example, when a nucleic acid sequence is being inferred from a known protein sequence, a collection of primers containing sequences representing all possible codon variations based on degeneracy of the genetic code will be used for each strand. One primer from this collection will be homologous with the end of the target sequence.

The method begins by preparing a double-stranded polynucleotide intermediate that contains the target sequence and additionally contains a promoter located upstream from the target sequence. This double-stranded intermediate is prepared by a series of steps using short oligonucleotides as primer sequences and extending the primers using the longer polynucleotide strand to which the primer binds as the template. The complementary target strand is obtained in a single-stranded state (if not already in that form) and is hybridized to an oligonucleotide sequence containing a promoter sequence upstream from a binding sequence complementary to a region in the complementary strand at or near the 3' end of the target region in the complementary strand. The binding sequence in this primer is substantially equivalent to a sequence in the target polynucleotide molecule found 5' to the specific target sequence being copied or at the 5' end of the target sequence. This primer is used to initiate the synthesis of a DNA molecule, using a DNA polymerase (such as reverse transcriptase), of the same sense as the original target strand.

A second oligonuncleotide is then hybridized to this newly synthesized strand. This second oligonucleotide primer is complementary to a region corresponding to the 3'-end of the target molecule. The number of nucleotides between the primer regions is preferably less than 300, more preferably less than 200, but more than 10, more preferably more than 15. When the second primer is extended, a copy of the target sequence and the first primer are formed. The resulting product, therefore, contains the promoter region 5' to the target sequence that is the object of this first part of the method of the invention.

The intermediate promoter-containing double-stranded polynucleotide is then used as a template for a DNA-dependent RNA polymerase capable of binding to the promoter region that has been created in the intermediate. The polymerase enzyme copies the target sequence, thereby providing multiple RNA copies of the target sequence downstream from the promoter. The number of copies produced depends on the promoter, the RNA polymerase used, and the reaction conditions, but 10 copies are readily produced and 100 or more copies can be prepared by selecting strong promoters, active RNA polymerases, and suitable reaction conditions.

Each of the RNA copies can be used as a template for the production of additional copies of the specific target. Reaction with the second oligonucleotide used above, extension of the primer to give the complementary sequence, reaction with the first primer and extension of the resulting hybrid in both directions (the first primer acting as primer for production of the target copy and the 3' terminus of the complementary strand acting as primer so that a copy of the promoter region is made) will produce a similar double-stranded promoter-containing intermediate described above that was used as a template for preparing RNA copies. RNA-producing cycles utilizing the promoter dependent RNA polymerase can then be repeated. If only 10 RNA copies are produced per cycle, three cycles will produce a one thousand-fold increase in the number of target sequences present in the reaction medium. If 100 copies of RNA are produced per template, one million copies of the target sequence will be produced by three cycles.

The method as described above assumes the presence of either a double-stranded polynucleotide target comprising a target strand and a complementary strand to the target strand or the presence of a complementary target strand if the initial target is a single-stranded polynucleotide, such as RNA. If the target is initially single-stranded RNA or DNA, the complementary target strand can be prepared in a manner similar to that described above using an oligonucleotide primer. For example, the second oligonucleotide primer described above is complementary to a region corresponding to the 3'-end of the target molecule. This second oligonucleotide primer, or a different primer complementary to a different region 3' to the target sequence, can be used to prepare the complementary strand used in the first step of the procedure. Another variation is to start with the oligonucleotide primer that is complementary to the target (rather than its complementary) strand. The promoter-sequence-containing primer is then hybridized to the complementary strand that is extended from the first primer.

The oligonucleotide primers are selected to be "substantially" complementary to the different strands of each specific sequence to be amplified. This means that the primers must be sufficiently complementary to hybridize with their respective strands. The primer sequence therefore need not reflect the exact sequence of the template to which it binds. For example, a non-complementary nucleotide fragment may be attached to the 5'-end of the primer, with the remainder of the primer sequence being complementary to the template strand. Of course, as described above, one such non-complementary nucleotide fragment will be a promoter sequence required by the invention. However, even when a promoter sequence is not present, other non-complementary nucleotide fragments may be attached. For example, a sequence providing a restriction endonuclease cleavage site can be provided to allow preparation of amplified target sequences ready for insertion into a plasmid. Alternatively, non-complementary bases can be interspersed in the binding sequence of the primer, provided that the primer sequence has sufficient complementarity with the sequence of the strand to be amplified (or its complementary strand) to hybridize therewith and form a template for synthesis of the extension product. For example, a single nucleotide can be replaced in a primer of moderate length (e.g., about 15 nucleotides) in order to provide a specific restriction endonuclease cleavage site.

If desired promoter sequences can be included in both primers to further multiply the number of copies produced by a complete cycle.

The operation of the method of the invention can be readily seen by reference to the Figure and the following more detailed description. Standard nomenclature and orientation are used for the schematic single- and double-stranded polynucleotides shown in the Figure and in the following discussion. The left end of the upper strand of double-stranded polynucleotides is the 5' end with the right end of the same strand being the 3' end (indicated by arrowheads). Since complementary strands have opposite orientations, the bottom strand is shown with its 3' end to the left and its 5' end to the right. In order to avoid confusion, the bottom strand is shown in this orientation even when not shown as part of a double-stranded polynucleotide. The same convention is followed for sequences set forth in the text (including the claims) in which the various sequences are identified by letters and numbers. Not all the products of each stage of the process are shown; only those relevant to this invention are illustrated.

In the first line of the Figure can be seen a double-stranded target polynucleotide molecule comprising a series of regions defined in terms of the operations that will be carried out on this molecule during later stages. As discussed previously, a double-stranded target is made for the initial step if the original target is a single-stranded RNA (or DNA) molecule. At the 5' end of the polynucleotide is a segment identified as X1 that will not be copied in later operations. This is followed by a segment of sequence P1 that comprises a part of the sequence of a primer used in a later stage. Sequence P1 is followed by target sequence T, which is the sequence being copied. A sequence P2, which binds with a different primer, is present at the 3' end of T. Additional nucleotides may be present past P2 but are not copied. These nucleotides are designated X2 in the figure. Neither X1 nor X2 are required for the operation of the present invention and are therefore optionally present, ranging in number from zero to many hundreds or even thousands of nucleotides. The apostrophe or "prime" designation indicates the complementary sequence present on the opposite strand. This double-stranded target molecule is denatured in the presence of an oligonucleotide primer and then conditions changed to allow annealing of the oligonucleotide and target as shown in line 2.

Line 2 of the Figure shows a first oligonucleotide primer, PR-P1, of complex structure but including the sequence P1 at its 3'-end, hybridized to the P1' segment of the denatured target molecule. The 5'-portion of this oligonucleotide primer, PR, contains a sequence which could, in its double-stranded form, comprise a functional promoter for an RNA polymerase. Sequence PR may contain additional nucleotides without adversely affecting the invention. The PR-P1 primer is extended by an appropriate enzyme (either a DNA-dependant DNA polymerase for a DNA target or a RNA-dependant DNA polymerase for a RNA and/or DNA target) to provide a strand, PR-P1-T-P2-X2 as shown in line 3 of the Figure. The single-stranded nature of the promoter region is designated in the Figure by the absence of contact between the two strands at this region and in the text in the following manner:

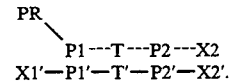

This (and other) primer of the invention is preferably relatively short, namely 50 or fewer nucleotides, in order to allow rapid hybridization (annealing) and cycling, especially with automatic equipment.

After denaturing the double-stranded polynucleotide shown in line 3 of the Figure, a second primer of sequence P2' is added to the mixture under annealing conditions as shown in line 4. Sequence P2' is equivalent to the sequence P2' previously identified and is itself complementary to the P2 segment of PR-P1-T-P2-X2.

Line 5 of the Figure shows the product obtained by extending the primer sequence P2' on the template shown. The promoter region at this stage is now double-stranded and therefore can be used for binding to a DNA-dependent RNA polymerase. In the text, this double-stranded intermediate is written:

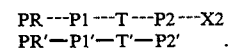

The copies produced by the RNA polymerase are shown in line 6 of the Figure. The copied segments, all downstream from the promoter region, are designated $P1^R$-$T^R$-$P2^R$ (the superscript R denotes an RNA copy). This RNA molecule can be the same as or slightly longer or shorter than P1-T-P2 since it will contain all of sequence PR-P1 at and after the initial nucleotide that is copied by the RNA polymerase. If the original target strand is a single-stranded DNA target, $P1^R$-$T^R$-$P2^R$ is the RNA equivalent of the original DNA plus any portion of the promoter-containing segment PR copied by the RNA polymerase or minus any nucleotides not copied by the polymerase.

If the RNA copies are to be recycled for additional amplification, the steps previously discussed for preparation of the promoter-containing double-stranded DNA intermediate are repeated. It is not necessary to use the same primer segments P1 and P2' or the same promotes segment PR, although PR-P1 and P2' are already available and can be used without modification. If other primer sequences are used, the resulting copies will be slightly shorter or larger than the first copies, but this does not adversely affect the invention unless there is some particular need or desire to retain the original P1-T-P2 sequence. Initial annealing with a P2' primer followed by extension of the primer provides the product shown in line 7 of the figure. Denaturation of the double-stranded intermediate and annealing with the primer PR-P1 provides the product shown in line 8. This intermediate can be extended in both directions since the P1 sequence acts as a primer using the complementary strand as a template and the complementary strand acts as a primer using sequence PR as a template.

If the same primers ace used in this step as were used in the steps indicated by lines 1 through 5, then the product will be similar to that shown in line 5, differing only in the extent of the top strand. This will not affect any subsequent RNA polymerizations as only the lower, template strand is used by the RNA polymerase. If different primer sequences are used the resulting template strand may be larger or shorter depending on the primers used. Provided that at least one of the primers used in this step has, at its 5'-end, a sequence representing a promoter for an RNA polymerase, the resulting material will still be capable of further amplification. Accordingly, the promoter-containing double-stranded DNA intermediate of line 9 in the figure can be used with DNA-dependent RNA polymerase to again produce multiple RNA copies.

When the initially used primers hybridize with unintended sequences in the DNA mixture containing the target molecule, advantages can be achieved by using different primers when the cycle is repeated. For example, if a particular target nucleotide is being detected in a crude analyte containing many polynucleotide sequences, such as when a bacterial or parasitic infection is being detected in a human fluid or tissue sample, hybridization of the primer oligonucleotides with host DNA can result in amplification of unintended host sequences. Since a promoter sequence will be present in the amplified background material, a significant increase in the amount of a specific background sequence is seen along with the increase in the target sequence. In order to avoid this problem, different primers and/or promoters can be used during different cycles to prevent amplification of the background. For example, a different binding region ($P1^x$ and/or $P2'^x$) that falls within the target sequence near or overlapping the binding region of the original primer can be used in the second cycle. Although there may be binding with other background polynucleotide sequences whose amplification is not desired, it is unlikely that the same background material would be amplified. The primers used in sequential steps can be described as being a nested set of primers, if this embodiment of the invention is followed, since successive pairs of primers would be found closer together on the complementary strands of the target molecule. The second (and successive) cycles can also use a different promoter region (e.g., $PR^x$) that binds a different RNA polymerase. Degradation of the first RNA polymerase remaining in solution followed by introduction of the second polymerase that binds to $PR^x$ will multiply the target copies but not the background copies, although an additional group of background copies may arise. Additionally, primers from earlier cycles, which may be present in excess, can be removed if desired. Suitable techniques for removing primers rely on characteristics that distinguish them from the target, such as size or the existence of the primers as single-stranded DNA when the target is present as double-stranded DNA or as RNA. For example, gel chromatography will remove small primers from larger targets while specific nucleases or antibodies will remove primers from double-stranded targets.

As an example of use of either the nested set of primers or different primers with different promoters, assume that in a first amplification cycle the desired target sequence is multiplied by a factor of fifty. At the same time, binding of primers to a background sequence occurs so that the background sequence is also multiplied by a factor of fifty. If the second amplification cycle uses nested primers and a fifty-fold multiplication again occurs, the target sequence will be multiplied by 2500 while (at worst) there will be two background sequences each multiplied by fifty. After three cycles of nested primers, the multiplication factor for target will be 125,000 with (at worst) three background sequences multiplied by fifty.

The individual steps of the method of the present invention are all conventional and can be carried out using known reagents and techniques. The only specially designed reagents are the primers PR-P1 and P2'. However, these segments can readily be obtained, either by total synthesis or isolation of the desired sequences from natural sources. Total synthesis is most readily practiced if the sequences P2 (and accordingly its complementary sequence P2') and P1 are known in the target molecule. Total synthesis of DNA segments containing promoter sequences is readily accomplished since promotes sequences themselves have been published. If the sequence of the target molecule is not known, the target molecule can be segmented by restriction endonucleases or other processes and segments selected for use in the invention. The RNA polymerase and its associated promoter sequence can be selected from the numerous available sources of these components. For example, T7 RNA polymerase from the T7 bacteriophage is available from New England Biolabs. Other RNA polymerases include SP6 from the bacteriophage SP6, available from New England Biolabs, or K-12 from E. coli strain K-12, which is available from Sigma Chemical Company, St. Louis, Mo. The corresponding promoters can be isolated from the organism from which the polymerase is obtained or synthesized chemically, where the promoter sequence is known.

Other biochemical reagents used in the method of the invention include an enzyme capable of extending primer sequences to form double-stranded polynucleotides. Such enzymes include reverse transcriptase and other DNA polymerases. Particularly preferred enzymes are AMV reverse transcriptase from LifeScience Inc. or polymerase I (Klenow fragment) from Bethesda Research Laboratories, Pharmacia, U.S. Biochemicals or Biolabs.

The individual steps of the present invention are readily adaptable to automation. Reactions can be carried out in a single container by sequentially adding reagents and changing conditions as necessary. Denaturing conditions generally involve increased temperatures, particularly temperatures in the range from 95° C. to 100° C. Annealing and primer extension occur at lower temperatures, typically 35° C. to 50° C. Since many proteins are denatured along with the polynucleotides at the higher temperatures indicated, additional proteins may be added as necessary. Other reagents present can include buffers to maintain the reaction at the appropriate pH and ionic conditions as well as mononucleotide triphosphates (eventually labeled or modified to provide a detectable signal) to be used in the extension reactions.

If high temperatures are used to denature double-stranded polynucleotides, there is no requirement of separating reagents or solutions. Other denaturing conditions, such as use of solvents, are less desirable because of the added separation steps when going from annealing to denaturing conditions and back to annealing conditions. However, numerous denaturing, annealing, and extending conditions are known and can be used if desired.

The multiple copies of the target sequence can be used in numerous ways. For example, the method of the invention can be used to prepare multiple copies of a gene for insertion into a plasmid or other target of a genetic engineering process. If used in a diagnostic assay for the target sequence, the detection step (hybridizing with a probe, reacting with an antibody or a specific ligand) can be carried out without isolating the amplified target from the reaction medium if the probe, antibody or ligand target is within the sequence T, i.e., does not encompass part of the primer or promoter regions. A probe target within the regions P1 and P2 can be selected, but separation of the target gene copies (P1-T-P2 or P1$^R$-T$^R$-P2$^R$) would be required in order to avoid binding with or interference by primer molecules. Labeled ribonucleoside triphosphates (e.g., radioactive labels, biotin or avidin labels) can also be used in steps in which RNA is produced. Additional uses of the polynucleotide products generated by this invention would include mutagenesis, genetic engineering and cloning, genetic analysis, therapy (both gene- and chemotherapy), the production of protein (both in vitro translation and introduction into cells), and any other processes benefitting from multiple copies of specific polynucleotide sequences. For example, RNA regulatory molecules can be produced in large amounts.

The invention now being generally described, the same will be better understood by reference to the following detailed examples which are provided for purposes of illustration only and are not intended to be limiting of the invention.

EXAMPLE

The techniques of the invention were assessed using a cloned gene of *Toxoplasma gondii*, specifically the thirty-five-fold repetitive antigen gene identifed as gene B1. The indicated gene was obtained from a recombinant DNA library containing inserts of genomic DNA from *T. gondii* (RH strain). The library was constructed in the expression vector lambda gt11 and was screened with antisera from an immunized rabbit. Recombinants thus identified were subcloned and further characterized. The target gene used in these studies was found to be part of a 2.2 kilobase-pair (kb) unit which is tandemly repeated many times in the genome of *T. gondii*. The identification and restriction map of this gene have been published (Boothroyd et al., "Antigen and Tubulin Genes of *Toxoplasma Gondii*", in Molecular Strategies of Parasitic Invasion, Ayabian et al., eds., UCLA Symposia Vol. 42, pp. 237–250, Alan Liss, New York, 1987). The nucleotide sequence of one complete repeat has been determined (but not published). The portion of the sequence relevant to the present work is reproduced below. The numbering system used measures from the EcoRI site defining the repeat in the genome. The sequence is shown as a double stranded molecule with the top strand being in the 5'-3' direction, left to right. The oligonculeotide segments are underlined in the strand of the same sense and thus the same sequence.

```
721
AAAAAATGTG  GGAATGAAAG  AGACGCTAAT  GTGTTTGCAT  AGGTTGCAGT  CACTGACGAG
TTTTTTACAC  CCTTACTTTC  TCTGCGATTA  CACAAACGTA  TCCAACGTCA  GTGACTGCTC
            OLIGO #0                            OLIGO #1

781
CTCCCCTCTG  CTGGCGAAAA  GTGAAATTCA  TGAGTATCTG  TGCAACTTTG  GTGTATTCGC
GAGGGGAGAC  GACCGCTTTT  CACTTTAAGT  ACTCATAGAC  ACGTTGAAAC  CACATAAGCG
                                                           OLIGO #2

841
AGATTGGTCG  CCTGCAATCG  ATAGTTGACC  ACGAACGCTT  TAAAGAACAG  GAGAAGAAGA
TCTAACCAGC  GGACGTTAGC  TATCAACTGG  TGCTTGCGAA  ATTTCTTGTC  CTCTTCTTCT
                                 OLIGO #3
```

Since the ultimate goal of the gene amplification was for potential use of the method in a diagnostic assay, the target gene was tested to see if it fit the remaining criteria necessary of a target gene for diagnosis. These are that the target gene be present in most of all strains of the parasite, not present in the genomes of other infectious agents (particularly those which might be confused in the diagnosis), and not detectable in the genome of the host. Preliminary investigations show that the gene is present in all strains of the parasite tested and that there is no cross-reactivity with the genomes of other organisms tested, including that of the human host.

A number of primers were evaluated for use in the method of the invention. These primers are identified by underlining in the sequence set forth above. The primers were 20–40 nucleotides (including the optional promoter sequence) in length showing homology with the target sequence for efficient annealing. A guanosine (G) or cytosine (C) residue was present at the 3' end of each primer to assure effective base pairing from which extension would occur. Primers were selected with no more than 150 base pairs between primers complementary to opposite strands so that extension would be efficient and rapid. The primers were further selected to lack the ability to form stable base-pair structures with other primers or within a single primer which would prohibit a primer from annealing to the target sequence. Although not essential to the multiplication steps, the primers were chosen to flank convenient restriction sites to facilitate cloning and construction of probes for the "internal" amplified DNA (i.e., a probe specific for the amplified product but which would not hybridize to the primers). The "internal" amplified DNA is equivalent to section T in the general description and claims.

The reaction conditions used for generation of the double stranded fragment including the T7 RNA polymerase promoter were similar to those previously described (Saiki et al., Nature (1986) 324:163-166). The reaction medium contained in a 100 μl volume, 10 mM Tris pH 7.5, 10 mM MgCl$_2$, 1.5 mM dNTPs, 1.5 μM oligonucleotide primers, and variable amounts of target containing DNA depending on the experiment (from 0.15 pg to 1.0 μg). Each cycle consisted of denaturation at 90° C. for 2 min (except for the first cycle, where denaturation occurred for 10 min), a quick chill on dry ice for 5 sec, a spin (to eliminate condensation at the top of the tube), annealing of primers at 35° C. for 2 min, addition of two units of Klenow fragments of E. coli polymerase I, and extension at 35° C. for 2 min.

The method of the invention was further carried out by including a promoter for the RNA polymerase of bacteriophage T7 at the 5' end of one of the target gene-specific oligonucleotides (oligo #1 identified above). The T7 promoter sequence is TAATACGACTCACTATAGGG. These additional 20 nucleotides were incorporated into the amplified double-stranded DNA products of the initial steps to provide products that are 20 bp larger than if oligonucleotides lacking this sequence were used. For example, the amplified DNA using oligos #1 and #2 is 117 bp, 20 bp larger than the 97 bp of the target including homology to the oligonucleotides (and similarly with oligos #1 and #3, the product was 151 bp=131 bp+20 bp).

These added-on sequences functioned as an efficient promoter for T7 RNA polymerase. The in vitro T7 transcription reactions were performed according to instructions of the supplier of the T7 RNA polyerase. The DNA template was taken directly from the reactions described above (which incorporated the promoter region) with no further treatment. An autoradiogram of the in vitro generated T7 RNA transcripts confirmed that they were 17 nucleotides shorter than the DNA template. In other words, the double-stranded DNA intermediate product of 151 base pairs gave a 134 nt RNA, 131 nt from target sequences and 3 nt (GGG) from the T7 promoter sequence. By incorporating [32P]-UTP into the RNA transcript, an approximately 3000-fold increase in the sensitivity of detecting amplified product was obtained as compared to ethidium bromide staining.

The assay of the invention was specifically designed to give high-specific-activity, low-yield RNA and therefore does not represent a maximum molar increase of target sequences generated from T7 transcription. However, it is known that under high-yield conditions, T7 RNA polymerase will produce between 50 and 100 RNA molecules per DNA template molecule (Davanloo et al., "Cloning and expression of the gene for the bacteriophage T7 RNA polymerase" Proc Natl Acad Sci. USA (1984) 81:2035-2039).

The procedure was carried out using several cycles of the T7RT amplification shown in the Figure and described above. This procedure is referred to here as the T7RT technique for convenience. This process has several advantages over the prior art PCR method. First, the target sequence to be amplified can be either RNA or DNA, which is important if the selected gene is highly expressed, since AMV reverse transcriptase can use either RNA or single-stranded DNA as a template. This is also relevant for applications in which the target sequences are exclusively RNA, as for retrovirus detection. Second, amplification from each full cycle, including both sequences, should be higher than with the PCR technique (up to 100 per cycle for T7RT compared with a maximum of 2 per cycle for the PCR technique) thus allowing a reduced number of cycles (3 cycles for a $10^6$-fold amplification for T7RT versus at least 20-25 for PCR) and the corresponding use of a smaller amount of enzyme. Third, large amounts of RNA can be produced for use in any process when RNA is preferable to DNA such as translation into protein, chemical lability, etc.

Initial investigations of the T7RT method utilized the same olgonucleotides and target sequences as described in the previous sections. As indicated in the Figure, two enzymes are used sequentially for each cycle: AMV reverse transcriptase and T7 RNA polymerase. Repeated steps of denaturation, annealing, and extension are realized by changes of sample temperature (90°-100° C. for denaturation, 37°-41° C. for annealing) and addition of enzyme to a sample containing nucleic acid to be amplified, adequate buffer (indicated by enzyme supplies), NTPs and dNTPs, molar excess of oligonucleotide primers, and an inhibitor of RNase.

In a first experiment, the gene fragment initially synthesized to contain a promoter sequence (as described above) was used to demonstrate the feasibility of the T7RT procedure. First, the substrate DNA was transcribed by T7 RNA polymerase, which was expected to yield an RNA product of 134 nt. This material was then converted back to a double stranded DNA as described and shown in the Figure using AMV reverse transcriptase in the presence of radio-labeled dNTPs. The major DNA product expected (and obtained) was also 134 nt, with a small amount of material of 151 nt present because of the continued presence of the input gene fragments. A control sample was similarly treated except that T7 polymerase was omitted. Following this reverse transcriptase step, a second cycle of direct amplification by AMV RT was performed on each sample. This resulted in the synthesis of substantial amounts of the 151 nt product by synthesis of the 134 nt product using oligo #1 (which has the extra 17 nucleotides of T7 promoter at its 5' end) as the primer. As the 134 nt material was about 10-fold more abundant (after one T7RT cycle) than the 151 nt product of the controlled reaction, the T7 amplification corresponded to that obtained by about 4.5 cycles of the PCR method alone. This amplification was achieved without optimizing the T7RT procedure, so that greater improvements in efficiency and cost over the PCR method are expected.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for increasing the number of copies of a target sequence, or the complement of said target sequence, in a polynucleotide sequence having a 3' region and a 5' region, and said target sequence therebetween, comprising the steps of:
   (1) preparing a first double-stranded DNA comprising a first promoter sequence upstream from said target sequence by:
      (a) contacting said polynucleotide sequence with a first primer able to bind to a region upstream of said target sequence,
      (b) extending said first primer with a DNA polymerase to form a primer extension product of said first primer having a sequence complementary to said target sequence,
      (c) making said primer extension product of said first primer available for hybridization with a second primer,
      (d) hybridizing said primer extension product of said first primer with a second primer able to bind to said primer extension product of said first primer at a region upstream of the sequence complementary to said target sequence, wherein one of said first and second primers comprises a 5' promoter sequence;
      (e) extending said second primer, and if necessary said primer extension product of said first primer, with a DNA polymerase to prepare said first double-stranded DNA comprising a first promoter,
   (2) transcribing multiple RNA copies from said first double-stranded DNA using a DNA-dependent RNA polymerase able to bind said promoter,
   (3) preparing a collection of second double-stranded DNA sequences comprising a second promoter by:
      (a) contacting said multiple RNA copies transcribed from said first double-stranded DNA with a third primer comprising a sequence able to bind to a region upstream of said target sequence, or the complement of said target sequence,
      (b) extending said third primer with an RNA dependent DNA polymerase to form a complementary DNA sequence comprising a primer extension product of said third primer comprising said target sequence or the complement of said target sequence,
      (c) making the primer extension product of said third primer available for hybridization with a fourth primer,
      (d) hybridizing said primer extension product of said third primer with a fourth primer able to bind to said primer extension product of said third primer at a region upstream of said target sequence, or the complement of said target sequence, wherein at least one of said third and fourth primers comprises a 5' promoter sequence, and wherein said third and fourth primers may be the same or different from said first and second primers, and
      (e) extending said fourth primer, and if necessary said primer extension product of said third primer, with a DNA polymerase to prepare said collection of second double-stranded DNA comprising a second promoter,
   (4) transcribing multiple RNA copies of said second double-stranded DNA using a DNA-dependent RNA polymerase able to bind said second promoter;
   (5) preparing a second collection of third double-stranded DNA comprising a third promoter by:
      (a) contacting said multiple RNA copies transcribed from said second double-stranded DNA with a fifth primer comprising a sequence able to bind to a region upstream of said target sequence, or the complement of said target sequence,
      (b) extending said fifth primer with an RNA-dependent DNA polymerase to form a complementary DNA sequence comprising a primer extension product of said fifth primer comprising said target sequence, or the complement of said target sequence,
      (c) making the primer extension product of said fifth primer available for hybridization with a sixth primer,
      (d) hybridizing said primer extension product of said fifth primer with a sixth primer able to bind to said primer extension product of said fifth primer at a region upstream of said target sequence, or the complement of said target sequence, wherein at least one of said fifth and sixth primers comprises a 5' promoter sequence, and wherein said fifth and sixth primers can be the same as or different from said first, second, third, and fourth primers, and
      (e) extending said sixth primer, and if necessary said primer extension product of said fifth primer, with a DNA polymerase to prepare said collection of third double-stranded DNA sequence comprising a third promoter.

2. The method of claim 1, wherein said first and second primers are the same as said third and fourth primers respectively, and as said fifth and sixth primers respectively.

3. The method of claim 1, wherein said transcribing multiple RNA copies from said first double-stranded DNA is performed without amplification of said double-stranded DNA.

4. The method of claim 1, wherein said third and fourth primers differ from said first and second primers respectively.

5. The method of claim 1, wherein said RNA dependent-DNA polymerase is reverse transcriptase.

6. The method of claim 1, wherein said DNA polymerase is reverse transcriptase.

7. The method of claim 5, wherein said reverse transcriptase is AMV reverse transcriptase.

8. The method of claim 6, wherein said reverse transcriptase is AMV reverse transcriptase.

9. The method of claim 1, wherein said method is performed in a single container by sequentially adding reagents and changing conditions as necessary.

10. The method of claim 1 wherein said reverse. transcriptase comprises RNase H activity active under conditions of said method.

* * * * *